(12) United States Patent
Rendon (10) Patent No.: US 7,494,643 B2
(45) Date of Patent: Feb. 24, 2009

(54) METHOD AND TOPICAL COMPOSITION FOR THE TREATMENT OF HYPERPIGMENTED SKIN

(76) Inventor: Marta I. Rendon, 1915 SW. 10th St., Boca Raton, FL (US) 33486

( * ) Notice: Subject to any disclaimer, the term of this patent is extended or adjusted under 35 U.S.C. 154(b) by 948 days.

(21) Appl. No.: 10/624,227

(22) Filed: Jul. 22, 2003

(65) Prior Publication Data
US 2005/0019282 A1    Jan. 27, 2005

(51) Int. Cl.
*A61K 9/00*    (2006.01)
*A61K 36/00*    (2006.01)

(52) U.S. Cl. .................. 424/62; 424/401; 424/725

(58) Field of Classification Search .................. 424/62, 424/401, 725
See application file for complete search history.

(56) References Cited

U.S. PATENT DOCUMENTS

| | | |
|---|---|---|
| 5,053,230 A | 10/1991 | Gazzani |
| 5,116,605 A | 5/1992 | Alt |
| 5,202,313 A | 4/1993 | Bombardelli et al. |
| 5,268,176 A | 12/1993 | Znaiden et al. |
| 5,358,716 A | 10/1994 | Laugier et al. |
| 5,391,550 A | 2/1995 | Carniglia et al. |
| 5,556,887 A | 9/1996 | Lerner |
| 5,607,980 A | 3/1997 | McAtee et al. |
| 5,637,304 A | 6/1997 | Salini |
| 5,665,364 A | 9/1997 | McAtee et al. |
| 5,738,856 A | 4/1998 | Korb et al. |
| 5,837,255 A | 11/1998 | Inman et al. |
| 5,851,543 A | 12/1998 | Korb et al. |
| 5,877,209 A | 3/1999 | Yunis |
| 5,962,517 A | 10/1999 | Murad |
| 5,998,485 A | 12/1999 | Tyan et al. |
| 6,106,850 A | 8/2000 | Simon et al. |
| 6,190,678 B1 | 2/2001 | Hasenoehrl et al. |
| 6,300,369 B1 * | 10/2001 | Ancira ....................... 514/460 |
| 2004/0137077 A1 * | 7/2004 | Ancira et al. ............... 424/616 |

FOREIGN PATENT DOCUMENTS

EP    2700268 A1 *    7/1994

(Continued)

OTHER PUBLICATIONS

Abstract—Sasson et al.; Growth and Bone Mineralisation as Affected by Dietary Calcium, Phytic Acid and Vitamin D; Comp Biochem Physiol A; 72(1); Jan. 1, 1982; pp. 43-48.

(Continued)

*Primary Examiner*—Lakshmi S Channavajjala
(74) *Attorney, Agent, or Firm*—Akerman Senterfitt; J. Rodman Steele, Jr.; Amy A. Dobbelaere (57) ABSTRACT

The present invention relates to novel, topically applied, cosmetic/dermatological compositions for the treatment of hyperpigmentation disorders and photodamaged human skin. The subject compositions combat hyperpigmented skin. In addition, the compounds described can be used in the treatment of many other pathologies. Due to a high degree of gentleness, along with potent antioxidant and moisturizing effects, the present invention can be used safely in the treatment of many conditions, such as the prevention and/or treatment of melasma, freckles, age spots (lentigo senilis) and photodamaged skin.

4 Claims, 5 Drawing Sheets
(3 of 5 Drawing Sheet(s) Filed in Color)

The Melanogenic Pathway.
Summary of the known biochemical reactions leading to melanin synthesis from tyrosine

FOREIGN PATENT DOCUMENTS

JP            200351722 A    * 12/2000
WO           WO 94/15626 A1  *  7/1994

OTHER PUBLICATIONS

Abstract—MacFoy et al.; Medicinal Plants in Pujehun District of Sierra Leone; J. Enthnopharmacol.; 8(2); Aug. 1, 1983; pp. 215-223.

Abstract—Jeziorek et al.; A Theoretical Study of the Mechanism of Oxygen Binding by Model Anthraquinones. Part II. Quantum-mechanical studies of the energetics of oxygen binding to model anthraquinones.; Anticancer Drug Des; 8(3); Jun. 1, 1993; pp. 223-235.

Abstract—Pollack et al.; Mechanism of Inositol Monophosphatase, the Putative Target of Lithium Therapy; Proc Natl Acad Sci USA; 21;91(13) Jun. 1994; 5738-9.

Abstract—Nakagawa et al.; Contact allergy to kojic acid in skin care products; Contact Dermatitis; 32(1); Jan. 1, 1995; pp. 9-13.

Abstract—Atack et al.; Inositol Monophosphate—a putative target for Li+ in the treatment of biopolar disorder; Trends Neurosci; 18(8); Aug. 1, 1995; pp. 343-349.

Abstract—Kroser et al.; Risk factors for the development of colorectal carcinoma and their modification; Hematol Oncol Clin North Am; 11(4); Aug. 1, 1997; pp. 547-577.

Abstract—Bravo; Acido Kojico: Un Neuvo Despigmentante; Rev. Chilena Dermatol.; 13(3); 1997; pp. 186-189.

Abstract—Pugliese et al.; The Skin's Antioxidant Systems; Dermatol Nurs; 10(6); Dec. 1, 1998; pp. 417-418.

Abstract—Fuller et al.; Vismiaphenones D-G, new prenylated benzophenones from Vismia cayennensis; J Nat Prod; 62(1); Jan. 1, 1999; pp. 67-69.

Abstract—Lim; Treatment of Melasma using Kojic Acid in a Gel Containing Hydroquinone and Glycolic Acid; Dermatol Surg; 25(4); Apr. 1, 1999; pp. 282-284.

Abstract—Jin et al.; Aloesin and arbutin inhibit tyrosinase activity in a synergistic manner via a different mechanism of action; Arch Pharm Res; 22(3); Jun. 1, 1999; pp. 232-236.

Abstract—Nickel et al.; Inositol hexaphosphate reduces 12-O-tetradecanoylphorbol-13-acetate-induced ornithine decarboxylase independent of protein kinase C isoform expression in keratinocytes; Cancer Letters; 140(1-2); Jun. 1, 1999; pp. 105-111.

Abstract—Ishikawa et al.; Inhibition of skin cancer by IP6 in vivo: initiation-promotion model; Anticancer Res; 19(5A); Sep. Oct. 1999; pp. 3749-3752.

Abstract—Barker et al.; Inositol hexakisphosphate and beta-cell stimulus-secretion coupling; Anticancer Res; 19(5A); Sep. Oct. 1999; pp. 3737-3741.

Abstract—Shamsuddin; Metabolism and cellular functions of IP6: a review; Anticancer Res; 19(5A); Sep. Oct. 1999; pp. 3733-3736.

Abstract—Jenab et al.; Phytic acid in wheat bran affects colon morphology, cell differentiation and apoptosis; Carcinogenesis; 21(8); Aug, 1, 2000; pp. 1547-1552.

* cited by examiner

Figure 1. The Melanogenic Pathway.

Summary of the known biochemical reactions leading to melanin synthesis from tyrosine FIGURE 2
Possible approaches to interfere with melanogenic pathway

METHOD AND TOPICAL COMPOSITION FOR THE TREATMENT OF HYPERPIGMENTED SKIN

BACKGROUND OF THE INVENTION

The present invention contains a unique combination of active ingredients for topical application. Together, these compounds seem to potentiate their effects and work in a synergistic matter. In addition, the composition of the present invention is prepared in a topical delivery system that enhances skin penetration. The composition is particularly useful for treating hyperpigmentation disorders such as melasma, postinflamatory hyperpigmentation, irregular pigmentation secondary to photodamage, lentigenes (age-spots) and others. The composition is nonirritating to the skin and also provides improved facial skin feel benefits. The unique blend is also useful for conditioning, desquamating, and cleansing the skin. The formulation can be in the form of a leave-on product and/or can be rinsed or wiped from the skin after use. The base uses special preservatives and antioxidants to achieve optimal bioavailability. The unique blend is compromised of *vismia* and inositol hexaphosphate (phytic acid). Additional ingredients, such as arbutin and kojic acid, may also be included in formulations of the present invention. The overall benefits include lightening pigmentation, providing even skin color and tone, improvement in photodamage and increased clarity. Added benefits include improvement in skin smoothness, radiance and moisture retention.

Cosmetic Interest in Depigmentation and Inhibition of Melanogenesis

The use of skin-lightening cosmetics varies significantly between cultures. In western countries, for example, skin lighteners are applied for the prevention and/or treatment of melasma, freckles and age spots (lentigo senilis). The treatment of irregular hyperpigmentation to reach an even skin tone is, doubtless, the main indication. In Asian and African nations, on the other hand, the primary use of skin lighteners is to make the skin whiter, lighter and brighter. Interestingly, while a tanned look is preferred in the West, most Asian people desire lighter skin. Traditional Asian beliefs hold that white skin denotes nobility and aristocracy. The present invention fulfills the demand of a broad range of these different applications in all continents.

Pigmentation

Pigmentation in animals varies greatly. It is often strikingly beautiful. In birds, most feather coloration is due to the presence of carotenoic pigments. In contrast, most visible pigmentation in mammals results from the synthesis and distribution of the pigment melanin. Chemically, melanins are heterogeneous biopolymers produced by specialized dendritic cells, the melanocytes, which are located primarily in the skin, hair bulbs and eyes. The process by which melanin is formed is known as melanogenesis.

Visible pigmentation in mammals results from the synthesis and distribution of melanin in the skin, hair bulbs and eyes. Tanning, a common and often desired phenomenon in many areas of the world, is simply the result of enhanced melanin production by the skin.

Melanin, the Skin Pigment

Melanin production occurs in the skin within specialized cells known as melanocytes. These cells originate from the neural crest and, during embryogenesis, migrate to various sites throughout the body, including the skin. There they become associated either with the hair follicles or the basal layer of the epidermis.

Epidermal melanocytes are thin, elongated dendritic cells with specific organelles, the melanosomes, which contain all components required for melanin production. The melanocytes, which extend and branch among neighboring epidermal cells, facilitate the transfer of melanosomes. The melanosomes are passed to keratinocytes in skin and to the hair shaft in hair bulbs, where the final distribution patterns of the pigment are determined. This distribution plays an important role in determining color and causes the great variety of colors that occur in the skin, hair, and eyes of humans. In this way, melanin is distributed into the suprabasal regions of the epidermis, where it protects the germinative cells of the basal layer from ultraviolet radiation.

In the human epidermis, each melanocyte is normally associated with approximately thirty-six (36) keratinocytes, together they constitute the epidermal melanin unit. Although melanocyte density varies quite considerably in different regions of the human skin, the total number is relatively constant, even in different racial groups. The average density is between 1'000 and 2'000 melanocytes/cm$^2$ skin.

Melanin plays a crucial role in the absorption of free radicals generated within the cytoplasm and in shielding the host from various types of ionizing radiation, including ultraviolet (UV) light. Thus, melanin protects the skin against sunburn, actinic damage and cancer. Moreover, melanin can act as a thermoregulator by absorbing different forms of energy and dissipating them as heat. Melanins are comprised of two basic types: eumelanins, which are brown or black, and phaeomelanins, which are red or yellow. In mammals, mixtures of both types are typically found. Interestingly, phaeomelanin has the capacity to produce free radicals in response to UV radiation. Since free radicals can inflict cell injury, phaeomelanin may actually contribute and intensify UV-induced skin damage, rather than protect the skin.

Figure 1:
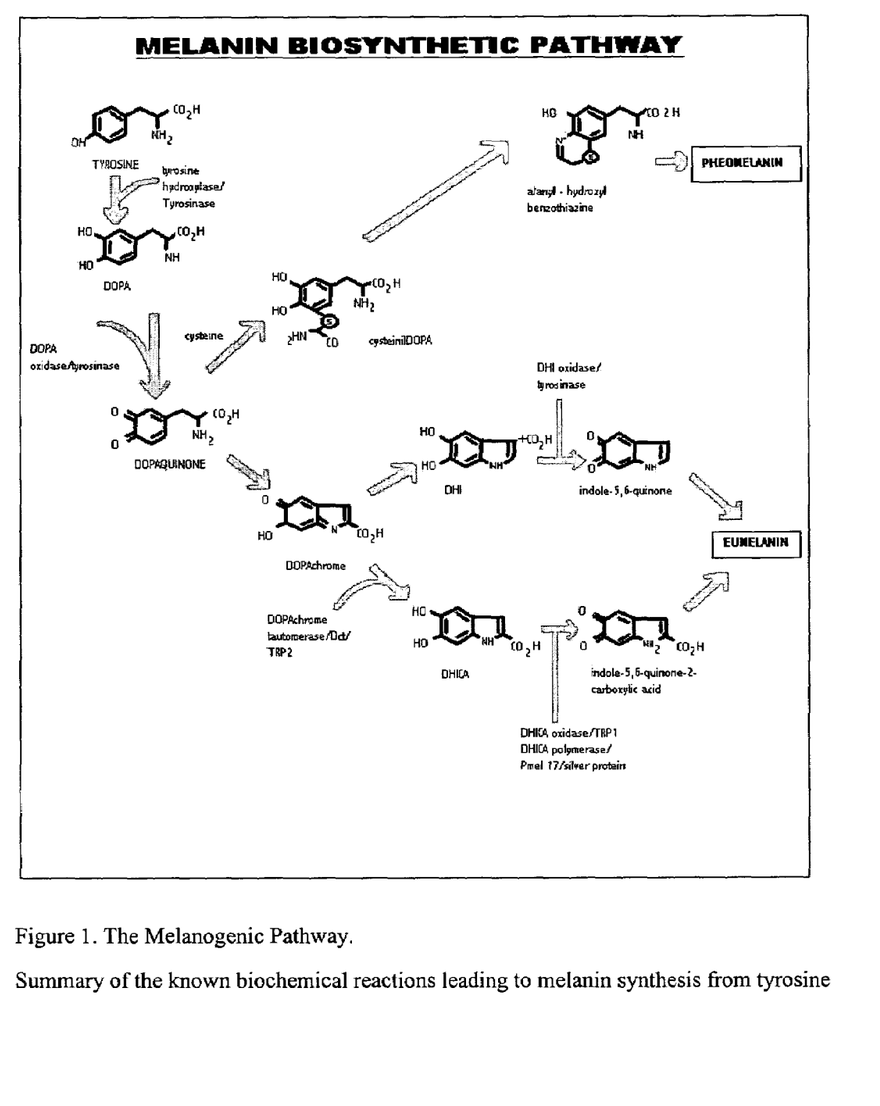
FIG. 1. The Melanogenic pathway. Summary of the known biochemical reactions leading to melanin synthesis from tyrosine.

Melanogenesis Overview (FIG. 1)

The initial compound for the production of melanin, both the brown-black eumelanin and the yellow-red pheomelanin, is the amino acid tyrosine. The quantity of melanin synthesized is thus proportional to the amount of tyrosine activity present in the cell. Melanin synthesis starts with the hydroxylation of tyrosine to 3,4-dihydroxyphenylalanine (L-DOPA) (see FIG. 1). This hydroxylation is the rate-limiting step in the melanogenesis pathway and is catalyzed by the key regulatory enzyme: tyrosinase. In humans, evidence indicates that human skin color can be correlated with tyrosinase activity.

Tyrosinase is the rate-limiting, essential enzyme in the biosynthesis of the skin pigment melanin. As such it catalyzes three different reactions in the biosynthetic pathway of melanin:

The hydroxylation of tyrosine to 3,4-dihydroxyphenylalanine (DOPA)

The oxidation of DOPA to DOPA-quinone

The oxidation of 5,6-dihydroxyindole (DHI) to indole quinone

Tyrosinase is a multi-functional, glycosilated, copper-containing oxidase with a molecular weight of approximately 60 to 70 KDa. In mammals, it is exclusively found in melanocytes. It is therefore a good marker for melanocytes. Tyrosinase is encoded by a gene at the c-locus that maps the chromosone 11q-14-q21 in humans and chromosone 7 in mice.

Tyrosinase is expressed specifically in pigment-producing cells. Expression of tyrosinase is regulated by cyclic AMP (cAMP). Tyrosinase is formed within the Golgi apparatus of the melanocyte by melanosomal ribosomes, tyrosinase glycosilation occurs in the endoplasmic reticulum in route to the TNGN (Trans-Golgi Network) and is transferred to the melanosome in its first stage of development (Stage I). Tyrosinase and additional proteins are assembled in Stage II melanosomes.

The molecular basis of Oculocutaneous Albinism (OCA) results from mutations in the genes that encode tyrosinase. In OCA type 1A, mutations in both copies of the tyrosinase-encoding gene lead to complete loss of enzyme activity, no melanin is found in the hair, skin or eyes, also known as albinism.

Recent studies have shown that mammalian melanogenesis is not regulated solely by tyrosinase at the enzymatic level and additional melanogenic factors have been identified, which can modulate pigmentation in either a positive or negative way. They have been called Melanogenesis-Related Proteins (MRPs) and are structural proteins involved in the formation of melanosomes together with the enzymes involved in the transformation of L-tyrosine to melanin: tyrosine in addition to tyrosinase related protein-1 ("TRP-1"), tyrosinase related protein-2 ("TRP-2"), gp 100 and PMEL 17, MART-1/Melan-A, P-protein MITF and MSH receptor.

The rate limiting steps in melanogenesis are the hydroxylation of tyrosine in the initial chemical reaction (conversation of tyrosine to DOPA), and the oxidation of DOPA by DOPA oxidase/tyrosinase (see FIG. 1) in the second reaction. In the last thirty (30) years, it has been demonstrated that there are additional control points in the melanin biosynthetic pathway. An example is the reaction that occurs when DOPAchrome is converted to 5,6-dihyroindole-2-carboxylic acid (DHICA) by TRP-2, also known as dopachrome tautomerase.

Dopaquinone is converted by a series of complex reactions involving cyclization and oxidative polymerization, which finally result in the formation of eumelanin. It was once thought that these latter reactions occurred spontaneously, but it now appears that certain steps are under regulatory control. For instance, there is now evidence that dopachrome can be converted to either 5,6-dihydroxyindole or the carboxy derivative 5,6-dihydroxyindole carboxylic acid (DHICA). The latter step appears to be catalyzed either by metal ions or by a recently discovered enzyme, dopachrome tautomerase, also known as TRP-2.

Dopachrome tautomerase occurs in melanosomes complexed with tyrosinase and perhaps other melanosomal membrane proteins. In addition, peroxidases can utilize DHI as a substrate and thus may also play a role in melanogenesis.

Another control point in the melanin biosynthetic pathway involves Tyrosine-Related Protein 1 (TRP1). Mutations in both copies of the TRP1 gene lead to OcularCutaneous Albinism (OCA) type 3, resulting in partial melanin loss. In mice and humans, TRP1 stabilizes tyrosinase and also in mice functions as DHICA oxidase.

The switch of the synthetic pathway from eumelanin to phaeomelanin requires the presence of sulphydryl residues. Thus, if dopachrome encounters either cysteine or glutathione, cysteinyl DOPAs are formed. These are then quickly oxidized into benzothiazines and subsequently to phaeomelanins.

Regulation of Melanogenesis

The regulation of pigmentation in mammals is controlled at many different levels and is quite complex at each level. Melanocytes are initially derived from the neural crest and migrate throughout the embryo during development. These migration patterns are under strict genetic control and can lead to some interesting patterns when the final melanocyte distribution in the skin is not uniform, as can be seen in zebras and giraffes. Pigmentation is also regulated at the cellular level by melanocytes synthesizing melanin within melanosomes, which can be produced in varying sizes, numbers and densities. Lastly, melanogenesis is regulated at the subcellular level where the synthesis and expression of various melanogenic enzymes and inhibitors play a critical role.

Skin pigmentation depends upon the organization and functioning of the epidermal melanin unit and several separate, but related, events:

Melanoblast migration from the neural crest
Melanoblast differentiation into melanocytes
The rate of synthesis and melanization of melanosomes
The size of melanosomes
Synthesis of melanin
The efficacy of melanosome transfer into keratinocytes
The rate of melanosome degradation within the keratinocytes
The rate of synthesis, inhibition and decay of tyrosinase
Activity of tyrosinase in melanosomes Melanocytes work in close harmony with their neighboring cells in the epidermis. They are influenced by a variety of biological factors, including interleukins, interferons, growth factors, vitamins and prostaglandins, which determine not only whether melanin is synthesized, but also what type of melanin is produced. Presumably, these factors provide the complex signals that stimulate pigmentation after trauma, UV-exposure, or other environmental stimuli that induce the melanocyte-stimulating hormone (MSH, or melanotropin), a peptide produced by the posterior pituitary. Once MSH binds to melanocyte surface receptors, a dramatic, up to 100-fold, increase in melanogenesis results.

Figure 2:
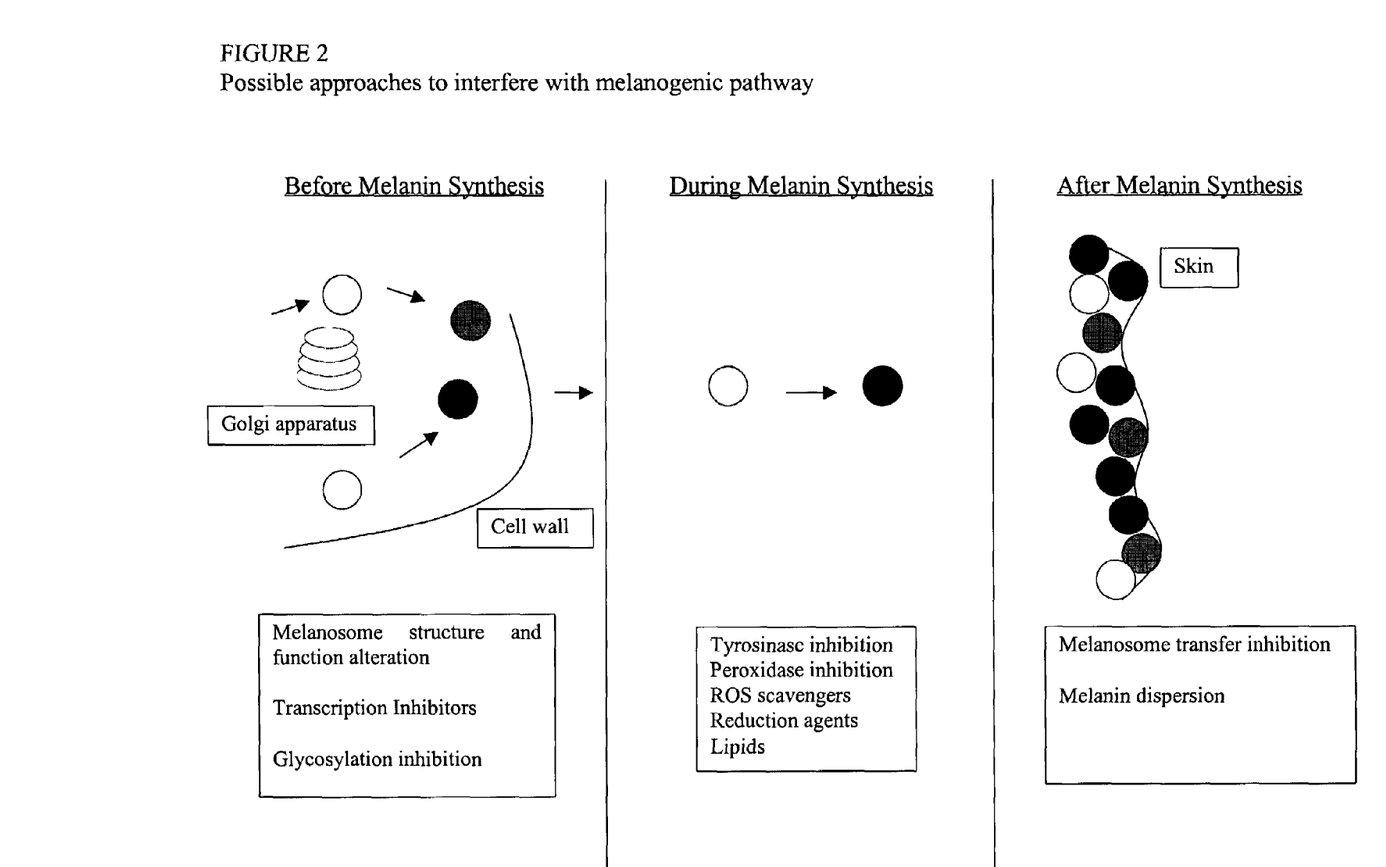
FIG. 2. Possible approaches to interfere with melanogenic pathway.

Melanogenesis can be affected at three different time intervals (see FIG. 2):

1. Before melanin synthesis by inhibiting transcription or glycosilation of the enzymes, thereby producing an alteration of the structure or function of the melanosome;
2. During melanin synthesis and when melanosomes are mature, peroxidase, ROS scavengers, reduction agents and/or lipids directly inhibit tyrosinase. This would affect the uptake and distribution of melanosomes in recipient keratinocytes.
3. After melanin synthesis, melanin and melanosome degradation occurs, increasing turnover of pigmented keratynocytes. Any blockage at this level would inhibit melanosome transfer and dispersion of melanin.

Recent work on molecular mechanism regulating pigmentation suggests that cAMP PKA (cyclic AMP dependent protein kinase) is the second major intracellular signaling molecule critical for skin pigmentation. PKC β (protein kinase C beta) is a key activator of tyrosinase, acting through phosphorylation of the protein at the cytoplasmic domain. Data suggest that this might be the rate limiting step. Cross talk between C-AMP and PKC affects pigmentation by up-regulating the expression of PKC-β.

The cyclic AMP pathway plays an important role in the production of melanin and the regulation of melanogenesis. The cyclic AMP pathway in melanocytes is activated by: ACTH, α-MSH, endothelin 1, nitrous oxide (NO) and PGE2. At the end product site, in response to UV stimulation, the keratinocytes secrete factors, such as interleukin 1α, interferon and TNFα. These factors inhibit melanogenesis.

Inositol Mechanism of Action

The nature of trying to lighten skin requires the use of new agents or means with little to no toxicity.

Inositol exists in plants as phytic acid (inositol hexaphosphate) and is also present in avian and fish erythrocytes, where it plays a role in allosteric regulation of oxygen affinity to hemoglobin. Inositol is an essential element in many species, including humans.

Biologically, inositol is an essential component of the cell membrane and is a key component of the multiple system intracellular signaling pathways and has also been implicated in key roles in the immune system.

Inositol functions on the site-specific signals on the cell membrane activating proteins for the assembly of spatially localized functional complexes, including signal transduction, cytoskeletal and membrane trafficking events with subsequent formation of specific proteins.

Although inositol has been implicated in many different functions and uses, it has not been described or used as a lightening agent. Its effect on pigmentation or melanogenesis has not been reported or documented.

We believe that inositol is a new lightening agent and works by affecting melanogenesis, acting in the melanin pathway.

Inositol may act in the melanogenesis pathway as an inhibitor through several different mechanisms. For example, it is possible that inositol acts as a transcription inhibitor by increasing the amount of dose-dependant intra-cellular free calcium ($Ca^{++}$) in the endoplasmic reticulum, where tyrosine is glycosilated. This would result in faulty protein production affecting the function and structure of the melanosomes.

Once melanin is glycosilated at the endoplasmic reticulum, the formed proteins are transported in vesicles to the TGN (Trans-Golgi Network) and from the TGN to the melanosomal compartment. A number of proteins help in the formation and transport of these vesicles including guanosine triphosphate-binding proteins, such as rab7 and phosphatidyl inositol kinase. Phosphatidyl inositol also regulates the membrane trafficking of melanosomal glycoproteins, controlling the production of melanin by down-regulating its substrate.

It is also possible that inositol acts as a post-transcriptional inhibitor of melanogenic enzymes at the N-glycosilation level. This would affect the protein structure of these enzymes and eventually the intracellular transport of the melanosome, reducing the level of its expression.

As mentioned earlier, melanogenesis results from a variety of regulatory processes involving direct effects of UV radiation on the melanocyte and indirect effects through the release of its final product (down-regulation). One of the intracellular signalling pathways is cyclic AMP. This pathway plays an important role in the production of melanin and the regulation of melanogenesis. The cyclic AMP pathway in melanocytes is activated by: ACTH, a-MSH, endothelin 1, nitrous oxide (NO) and PGE2. At the end product site, in response to the UV stimulation, the keratinocytes secrete factors, such as interleukin 1α, interferon and TNFα. These factors inhibit melanogenesis. Inositol hexaphosphate increases cyclic AMP and thereby decreases the production rate of melanin. A balance between these keratinocyte factors permits melanocyte growth and differentiation, ultimately controlling skin pigmentation.

BRIEF SUMMARY OF THE INVENTION

*Vismia*, phytic acid, arbutin, and kojic acid all have depigmentation properties that are beneficial in dermatological applications. Phytic acid, arbutin and kojic acid act in the tyrosine metabolic pathway by different mechanisms. *Vismia* utilizes a mechanism of action similar to an anthraquinone, where it competes with the tyrosinase substrate. *Vismia*, phytic acid, arbutin and kojic acid provide suitable substitutes for hydroquinone, which has been utilized in the last decade as a skin lightening agent, but has been reported to create adverse effects in many who use it. For this reason, the use of hydroquinone in over-the-counter formulations has been banned in Europe and Japan. The topical use of *vismia*, phytic acid, arbutin and kojic acid impacts the final melanin distribution in human skin.

*Vismia*, phytic acid, arbutin and kojic acid can be used for the prevention and/or treatment of melasma, freckles or age spots (lentigo senilis). They can also be utilized in programs designed for superficial peeling, utilizing phytic acid in combination with arbutin and kojic acid in the concentrations proposed.

It has been explained earlier that oxidative stress damages cellular elements, which can be repaired with most known antioxidants, such as Vitamin C. Unfortunately, to combat all sources of oxidative stress, it is necessary to use a large number of different antioxidants. The present novel approach of the combination of *vismia* and phytic acid combats free radicals that are produced during the normal process of cellular metabolism. Phytic acid is a very potent antioxidant and is used in the industry as an anti-rust and anti-corrosion agent for metals, chelating agents for removal of metal ions, coating additive, contrast agent, developing agent, fermentation promoter, fuel anti-knock agent, gathering agent for rare earth and precious metals, high molecular solvent, oral cleansing agent, preservative, stabilizer, water treatment agent.

We have shown how *vismia* and phytic acid independently both have lightening effects on the skin. The moment *vismia* and phytic acid are utilized in the proposed combinations, the protection of the skin has consequences never seen in the history of dermatological care. The addition of other known skin lighteners, such as arbutin and kojic acid, provides additional benefits.

The present invention combines *vismia* and inositol in a novel formulation to better provide skin lightening. A brief description of these and several other ingredients of the formulation follows in the Detailed Description of the Invention.

The industry is in need of a non-hydroquinone lightening agent which has no toxicity, minimal side effects and good long term effect.

BRIEF DESCRIPTION OF THE FIGURES

The patent or application file contains three color photographs. Copies of this patent or patent application publication with color drawings will be provided by the Patent and Trademark Office upon request and payment of the necessary fee.

DETAILED DESCRIPTION OF THE INVENTION

Throughout the claims and specification, the terms "inositol" and "phytic acid" are used interchangeably and include the salts and esters of the same.

Throughout the claims and specification, the term "topical" includes any currently known or future developed vehicles of administration through human skin, including, but not limited to, solution, cream, lotion, gel, patch, spray, emulsion, and the like.

Throughout the claims and specification, the terms "hyperpigmentation disorder" and "hyperpigmented disorder" are used interchangeably to refer to melasma, postinflamatory hyperpigmentation, irregular pigmentation secondary to photodamage, lentigenes (age-spots), and drug induced hyperpigmentation.

The present invention utilizes a combination of *vismia* and inositol to treat hyperpigmentation disorders such as melasma, postinflamatory hyperpigmentation, irregular pigmentation secondary to photodamage, lentigenes (age-spots) and others. Additional ingredients, such as arbutin, kojic acid, antioxidants, and quinones may be included in formulations of the present invention. The formulations of the present invention may take any known topical forms, including, but not limited to creams, ointments, gels and the like. Some information on the individual ingredients is presented below:

A. *Vismia*

*Vismia* spp. are trees or tall shrubs growing primarily in the tropical and subtropical regions of South and Central America, with a few species also found in Africa and Asia. Of the roughly fifty *Vismia* spp known, fifteen are found in Venezuela. The latex from *Vismia anhusta* is used by many Indian tribes of the Colombian Amazonia to treat wounds and infected sores and is used by the Tikunas to treat fungus and herpes. A tea from *Vismia confertiflora* is used by the Yakunas and Makunas of the Miritiparana and Popeyaka Rivers as a diuretic. The same tribe of *Vismia dealbata* is used by the Puinaves to treat skin diseases (maladies) from fungal origin. The resin from *Vismia Ferruginea* is applied to wounds in the Colombian, Brazilian and Peruvian Amazonia. A mixture of leaves of *Vismia Guineensis* and *Canthium Glabriflorum* is used as a blood tonic for children in the Pejehun District of Sierra Leone, West Africa. *Vismia micrantha* has been used as a purgative, tonic, febrifuge and antireumathic agent. *Vismia latifolia* Choisy is well known in the Brazilian and Colombian Amazonia for its use as a febrifuge. An exudate of *Vismia tomentosa* is used by the Mikuna tribe to treat red skin rashes. The resin extracted from the tree of *Vismia angusta* is used for sores, skin infections, and for the treatment of ringworm or "caracha" (a fungal dermatosis). Amazonian Colombians use the latex for infected sores and wounds. Vismiaphenone D isolated from extracts of leaves of *Vismia Cayennensis*, has HIV-inhibitory activity in the NCI primary screen. The pounded yellowish-red resin from *Vismia Guineensis* makes an ointment for craw-craw; the sap is reportedly applied to circumcision wounds in Sierra Leone.

Vismin was isolated from *Vismia macrophyla*. No prior study has described the use of *Vismia* and its compounds or the activity of its extracts, nor is there any suggestion that anthracenone compounds, such as vismin, are useful as hypopigmentation agents. Among the sixty known species, more than fifteen species of *Vismia* have been investigated; the chemistry of the Guttiferae family has been widely studied. Several species from this genus have been shown to contain anthranoids and xanthones. Anthraquinones, Vismiaquinone C and Vismiaquinone (Benzophenones) have been identified as chemical constituents of *Vismia parviflora*. Vismiaquinones have also been isolated from *Vismia Latifolia*, whose use in the Brazilian and Colombian Amazonia for dermatological purposes is quite popular.

The compositions of the present invention yield optimal results with between one (1) and five (5) percent by weight *vismia* and/or its derviates, based on the weight of the total composition.

B. Inositol

Inositol, as a hexadroxy alcohol, is present in plasma membranes and is the source of second messengers that are involved in the action of some hormones throughout the body controlling the secretion of hormones such as gonadotropes and testosterone.

Inositol hexaphosphate has a demonstrably anti-cancer action against a variety of tumors.

Phytic acid, also known as inositolhexaphosphoric acid and found in grains, can reduce calcium absorption. Large quantities of refined sugar, caffeine and soda drinks can increase calcium excretion. Phytic acid acts as a chelating agent due to its six reactive phosphate groups. It is a complex agent for removal of traces of heavy metal ions, acting also as a hypocalcemic agent. For its properties as a chelating agent for calcium and for augmenting and hardening the dentist cement, phytic acid is employed in dentistry including dental creams and chewing gums. Phytic acid also modulates the release of insulin from pancreatic cells by inhibiting serine/threonine proteins on calcium channels.

In vivo studies have shown the anticarcinogenic effects of phytic acid on skin cancer. Laboratory studies of phytochemicals, such as phytic acid, have demonstrated potentially important anticarcinogenic properties having an important chemoprotective role.

High-fiber diets are beneficial for its effects on preventing tumorigenesis. Phytic acid is a fiber-associated component of cereals and legumes and has been demonstrated to inhibit cell proliferation and enhance cell differentiation, indicating its chemoprotective role.

Wheat bran and its component, phytic acid, decreases colon carcinogenesis.

Phytic acid has an important role as a growth factor, reproduced in animal models.

Phytic acid is a physiological antioxidant with potential to form complexes with cations linked to cell proliferation and hypercholesterolemia. Antioxidants are produced by the skin to protect it against free radical attacks. Phytic acid is a specific antioxidant of reactive oxygen.

Phytic acid acts as a chelating agent due to its six reactive phosphate groups, it is a complex agent for removal of traces of heavy metal ions, acting also as a hypocalcemic agent.

It is known that phytic acid is a vital component of the cell membrane, where it constitutes a sea of lipids in a fluid state, in which lipids and proteins are able to move and interact. Phytic acid is depleted in photodamaged skin. It is reasonable to replace this deficiency in a convenient manner by incorporating phytic acid into moisturizers and dermatological products used by patients.

Phytic acid has great benefits correcting hyperpigmentation disorders such as melasma and post inflammatory hyperpigmentation. Because of its anti-inflammatory characteristics, phytic acid prevents post inflammatory lesions in the inflammatory phase of skin peeling at the third and fourth weeks, reducing tremendously the inflammatory process and consequently diminishing the chance of formation of hyperchromic marks from these peelings.

The compositions of the present invention yield optimal results with between one (1) and five (5) percent by weight inositol and/or its derviates, based on the weight of the total composition.

As discussed earlier, topical application of the combination of inositol and *vismia* provides unexpected results in the treatment of hyperpigmentation disorders such as melasma, postinflamatory hyperpigmentation, irregular pigmentation secondary to photodamage, lentigenes (age-spots) and others. The following ingredients provide additional benefits to compositions of the present invention.

C. Arbutin

Arbutin has been used in traditional medicine for cystitis as an urinary disinfectant and has been especially effective with alkaline urine caused by vegetarian diet. Arbutin alone has been reported to be an effective urinary antibiotic, but only if taken in large doses and if the urine is alkaline (once again documenting the value of whole plant medicines). It is reported to be active against *Candida albicans* and *S. aureus*, and especially active against *E. coli*. *Uva ursi* also has diuretic properties. Arbutin is hydrolyzed to hydroquinone and glucose in the body. Hydroquinone is most effective in an alkaline urine; however, crude plant extracts are more effective medicinally than isolated Arbutin. This appears to be related to the activity of gallic acid, which prevents the splitting of Arbutin by such enzymes as beta-glucosidase. *Uva Ursi* reported to be especially active against *E. coli*, also has diuretic effects. Arbutin is a medication with depigmentation properties. Arbutin inhibits tyrosinase, inhibiting melanin synthesis acting as a depigmentator. Arbutin inhibits tyrosinase activity in a synergistic manner by acting through a different action mechanism. Arbutin similarly inhibits enzyme activity of human- and mushroom-tyrosinases. Arbutin inhibits melanin production by competitive inhibition of tyrosinase activity. Arbutin is found in bearberry (*Arctostaphylos uva-urs*). It is extracted from the leaves of the plant, where arbutin is about 8% of the leaves, and methyl arbutin, flavinoids, phenolic acids, volatile oils and resins are the rest. *Uva ursi* is a small evergreen shrub found in the northern United States and in Europe. A single long, fibrous main root sends out several prostate or buried stems 4-6 inches high. The bark is dark brown, the leaves are obovate to spatulate and 0.5-1 inch long. The flowers are pink or white, growing in sparse terminal clusters. The fruit is a bright red or pink. This plant has a long history of use for its diuretic and astringent properties. Conditions for which it has been used include chronic cystitis, nephritis, kidney stones, and bronchitis.

Some early animal research is now showing that arbutin, and possibly other constituents of *uva ursi*, potentiate the activity of commonly prescribed anti-inflammatory drugs. One study found that an aqueous extract increased the inhibitory activity of dexamethasone in allergic and inflammatory models, without increasing any of the side effects. Similar results have been demonstrated with isolated arbutin when combined with indomethacin. Crude extracts are widely used in Europe as components in certain diuretic and laxative products.

The compositions of the present invention yield optimal results with between two (2) and four (4) percent by weight arbutin and/or its derviates, based on the weight of the total composition.

D. Kojic Acid

Kojic acid, like arbutin and phytic acid, has depigmentation properties. All three compounds have the same mechanism of action, acting in the tyrosine metabolic pathway, inhibiting tyrosinase. Kojic acid is a fungal metabolite produced by *Aspergillus* and *Penicillium* spp. It is structurally related to maltol. Like maltol, it is a good chelator of transition metal ions and has been shown to inhibit tyrosinase activity. Kojic acid was shown to inhibit tyrosinase isolated from black goldfish and standard goldfish and to suppress melanogenesis in cultured pigment cells. When kojic acid was ingested by the fish, the black goldfish became almost yellow-brown. Kojic acid improves hyperpigmentation disorders including facial melasma, freckles (lentigo aestiva) or age spots (lentigo senilis). It has been shown that kojic acid peels are less drying to skin than glycolic or salycilic acid.

The compositions of the present invention yield optimal results with between two (2) and four (4) percent by weight kojic acid and/or its derviates, based on the weight of the total composition.

E. Antioxidants

Antioxidants are scavengers of highly reactive oxygen species, the so-called free radicals, which are capable of degrading lipid constituents of cell membranes, proteins and DNA. Vitamin C and Vitamin E and, to a lesser extent, Vitamin A, are well known free radical scavengers. Superoxide dismutase is a natural protein with endogenous antioxidant properties.

Antioxidants play an important role in skin cosmetics. The skin is a very sensitive organ to all forms of harmful effects. More than any other tissue in the body, it is exposed to different changes in temperature and different types of radiation, which not only harm the skin but also induce the formation of free radicals, which reduce the natural antioxidants in the skin.

In normal conditions the cells of the body have antioxidant pools. Several types of antioxidants combat the production of free radicals physiologically.

Any lack of this equilibrium retains the production in the activity of this oxidant pool, determining an alteration of the cellular homeostasis, which is called oxidative stress. The oxidative stress causes deficiency of antioxidant molecules and also increases in the oxidants (free radicals). The consequences are irreversible destruction of the cellular membrane, nucleus, nucleic acids, DNA and RNA oxidation of other proteins and cellular enzymes. The hydroxyl radicals are especially set to begin the lipid perioxidation in the cell membrane forming secondary products. These secondary products are involved in the organic aging both internal and external in the carcinogens.

The oxidative stress is more important in several dermal diseases: heat induced lesions, ionized infrared radiation, psoriasis, photodermatosis, seborrheic dermatitis. The oxidative stress is equally implicated in a process that affects all of us: Both intrinsic and extrinsic aging.

The search for substances that decreases the process of aging of skin and other cells of the human body involves the knowledge of several substances that can act as destructor of those free radicals. The antioxidants can be used in this topical area or systemic. Vegetables receive both UVA and LVB radiations and constantly develop sophisticated methods to minimize the oxygen radicals (free radicals). There are many antioxidants in the grain, leaves or fruits, the wax around the leaves, the oil producing bean and herbs. It is interesting to note that the levels of antioxidants vary in the vegetables according of the season of the year. The prevention of oxidation in the sophisticated foods promotes the preservation of the food.

Other antioxidants that are encountered in vegetables include antioxidants of the tanino (present in the guadana-fruit and leaves). These antioxidants are encountered in the chips of eucalyptus and glucoside antioxidants of the wood encountered in the seeds of gerdalin. The research that has been going on about antioxidants are centered in the gathering analysis of materials from plants that exist in nature such as the compounds present in this invention. Phytic acid acts not only as an antioxidant but as an antiinflamatory agent, having hydrating properties which means that it can be used as a skin cleanser with a degree of sensibility like white skin and sensitive skin or skin that have suffered great aggressions by any other chemical or physical process.

F. Quinones

Anthraquinone is the most important quinine derivative of anthracene and quinine, and the parent substance of a large class of dyes and pigments. It is used in paper industry as a catalyst to increase pulp production. Sixteen new prenylated anthraquinones and xanthones have been isolated from *Vismia guineensis*.

Anthraquinone is also found in different plants such as Aloe Vera. The bitter juice contains anthraquinone glycosides and free anthraquinones resins. It as been used in bums, cuts and wounds. Anthraquinone is also known to bind free radicals resulting in antioxidant properties.

The reduction of quinone to the corresponding dihydroxy form is an important characteristic reaction that yields Hydroquinone that is used in dermatology as an antioxidant, inhibiting polymerization by direct reaction with peroxy-free radicals.

Quinones are also used as agents for skin lightening. Hydroquinone has been the standard dermatological depigmentation agent for the last forty years. Hydroquinone inhibits the tyrosinase enzyme. Although it is the current standard dermatological depigmenting agent, hydroquinone is cytotoxic in that it destroys the cellular walls of the melanocytes. Prolonged use of hydroquinone can also produce Ochronosis, a condition that gives skin a bluish/gray pigmentation, which is permanent in some cases. When topical compositions containing two percent or more of hydroquinone are used for more than sixty days, irreversible lesions may form, such as confetti lesions or residual acromia.

G. Formulations

The nature of trying to lighten skin requires the use of new agents or means with little to no toxicity. As discussed above, prolonged use of hydroquinone to lighten skin can result in irreversible damage. *Vismia*, phytic acid, arbutin and kojic acid provide a suitable substitute for hydroquinone. While arbutin and kojic acid are both documented depigmentation agents, neither agent alone provides the benefits achieved by the combination of *vismia* and phytic acid. Half face studies are currently in trial comparing the industry standard, hydroquinone, with compositions of the present invention. The expected result is a novel and non-toxic treatment of hyperpigmentation disorders such as melasma, postinflamatory hyperpigmentation, irregular pigmentation secondary to photodamage, lentigenes (age-spots) and others.

The invention will now be further described with reference to the following examples and figures, which are provided for illustrative and non-limiting purposes:

EXAMPLE 1

Skin Brightener Formula (One Embodiment of Present Invention)

| Ingredients | % (w/w) |
| --- | --- |
| Alpha/Arbutin | 1 |
| Ascorbic Acid | 1 |
| Cetearyl Alcohol | 3 |
| Citric Acid | 2 |
| Fragrance | 0.2 |
| Green Tea Extract | 1 |
| Water | 63 |
| Isopropyl Palmitate | 5 |
| Inositol Hexanicotinate | 4 |
| Kojic Acid Dipalmitate | 2 |
| Menthyl Lactate | 1 |
| Arachidyl Alcohol, Behenyl Alcohol and Arachidylglucoside | 0.3 |
| Preservative | 5 |
| Hyaluronic acid/Sodium Lactate | 0.3 |
| Propylene Glycol | 3 |
| Rumex Crispus Extract | 3 |
| Polyacrylamide & C13-14 isoparaffin and laureth-7 | 3 |
| Vismia | 2 |
| Vitamin E | 0.2 |

EXAMPLE 2

Skin Brightener Formula (Another Embodiment of Present Invention)

| Ingredients | % (w/w) |
| --- | --- |
| Alpha/Arbutin | 1 |
| Ascorbic Acid | 1 |
| Cetearyl Alcohol | 3 |
| Citric Acid | 2 |
| Fragrance | 0.2 |
| Green Tea Extract | 1 |
| Water | 67 |
| Isopropyl Palmitate | 5 |
| Inositol Hexanicotinate | 1 |
| Kojic Acid Dipalmitate | 1 |
| Menthyl Lactate | 0.4 |
| Arachidyl Alcohol, Behenyl Alcohol and Arachidylglucoside | 5 |
| Preservative | 0.3 |
| Hyaluronic acid/Sodium Lactate | 3 |
| Propylene Glycol | 3 |
| Rumex Crispus Extract | 3 |
| Polyacrylamide & C13-14 isoparaffin and laureth-7 | 2 |
| Vismia | 1 |
| Vitamin E | 0.1 |

EXAMPLE 3

Skin Brightener Formula (Another Embodiment of Present Invention)

| Ingredients | % (w/w) |
| --- | --- |
| Ascorbic Acid | 1 |
| Cetearyl Alcohol | 3 |
| Citric Acid | 2 |
| Fragrance | 0.2 |
| Green Tea Extract | 1 |
| Water | 63 |
| Isopropyl Palmitate | 5 |
| Inositol Hexanicotinate | 5 |

-continued

| Ingredients | % (w/w) |
| --- | --- |
| Menthyl Lactate | 1 |
| Arachidyl Alcohol, Behenyl Alcohol and Arachidylglucoside | 0.3 |
| Preservative | 5 |
| Hyaluronic acid/Sodium Lactate | 0.3 |
| Propylene Glycol | 3 |
| Rumex Crispus Extract | 3 |
| Polyacrylamide & C13-14 isoparaffin and laureth-7 | 3 |
| Vismia | 4 |
| Vitamin E | 0.2 |

EXAMPLE 4

Skin Brightener Formula (No *Vismia*)

| Ingredients | % (w/w) |
| --- | --- |
| Alpha/Arbutin | 2 |
| Ascorbic Acid | 2 |
| Cetearyl Alcohol | 3 |
| Citric Acid | 2 |
| Fragrance | 0.2 |
| Green Tea Extract | 1 |
| Water | 64 |
| Isopropyl Palmitate | 5 |
| Inositol Hexanicotinate | 3 |
| Kojic Acid Dipalmitate | 2 |
| Menthyl Lactate | 1 |
| Arachidyl Alcohol, Behenyl Alcohol and Arachidylglucoside | 0.3 |
| Preservative | 5 |
| Hyaluronic acid/Sodium Lactate | 0.3 |
| Propylene Glycol | 3 |
| Rumex Crispus Extract | 3 |
| Polyacrylamide & C13-14 isoparaffin and laureth-7 | 3 |
| Vitamin E | 0.2 |

EXAMPLE 5

Skin Brightener Formula (Control—No *Vismia*, No Inositol)

| Ingredients | % (w/w) |
| --- | --- |
| Alpha/Arbutin | 2 |
| Ascorbic Acid | 2 |
| Cetearyl Alcohol | 3 |
| Citric Acid | 2 |
| Fragrance | 0.2 |
| Green Tea Extract | 1 |
| Water | 66 |
| Isopropyl Palmitate | 5 |
| Kojic Acid Dipalmitate | 3 |
| Menthyl Lactate | 1 |
| Arachidyl Alcohol, Behenyl Alcohol and Arachidylglucoside | 0.3 |
| Preservative | 5 |
| Hyaluronic acid/Sodium Lactate | 0.3 |
| Propylene Glycol | 3 |
| Rumex Crispus Extract | 3 |

-continued

| Ingredients | % (w/w) |
| --- | --- |
| Polyacrylamide & C13-14 isoparaffin and laureth-7 | 3 |
| Vitamin E | 0.2 |

EXAMPLE 6

Skin Brightener Formula (Control—No Skin Lighteners)

| Ingredients | % (w/w) |
| --- | --- |
| Ascorbic Acid | 2 |
| Cetearyl Alcohol | 3 |
| Citric Acid | 2 |
| Fragrance | 0.2 |
| Green Tea Extract | 1 |
| Water | 71 |
| Isopropyl Palmitate | 5 |
| Menthyl Lactate | 1 |
| Arachidyl Alcohol, Behenyl Alcohol and Arachidylglucoside | 0.3 |
| Preservative | 5 |
| Hyaluronic acid/Sodium Lactate | 0.3 |
| Propylene Glycol | 3 |
| Rumex Crispus Extract | 3 |
| Polyacrylamide & C13-14 isoparaffin and laureth-7 | 3 |
| Vitamin E | 0.2 |

Figure 3:
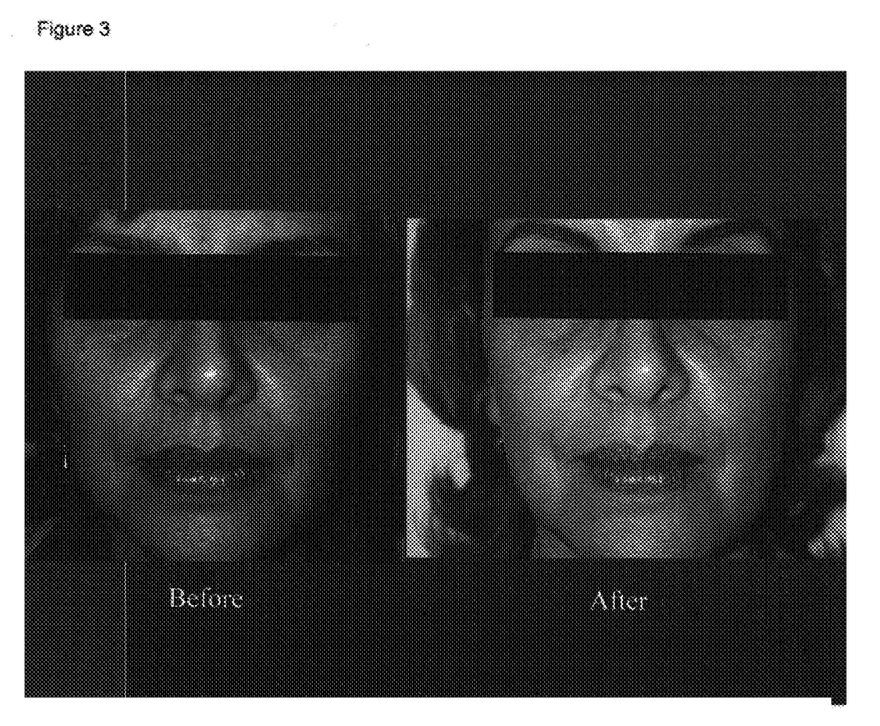
FIG. 3. Photographs taken before and after one month of topical application of a combination of *vismia* and phytic acid.
Figure 4:
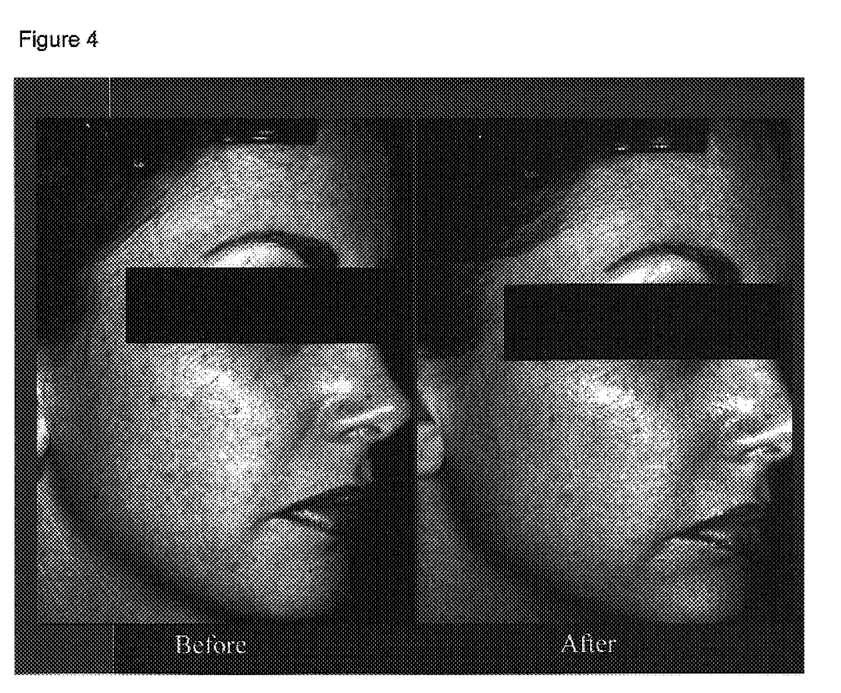
FIG. 4. Photographs taken before and after application of a control substance, which contained neither *vismia* nor inositol.
Figure 5:
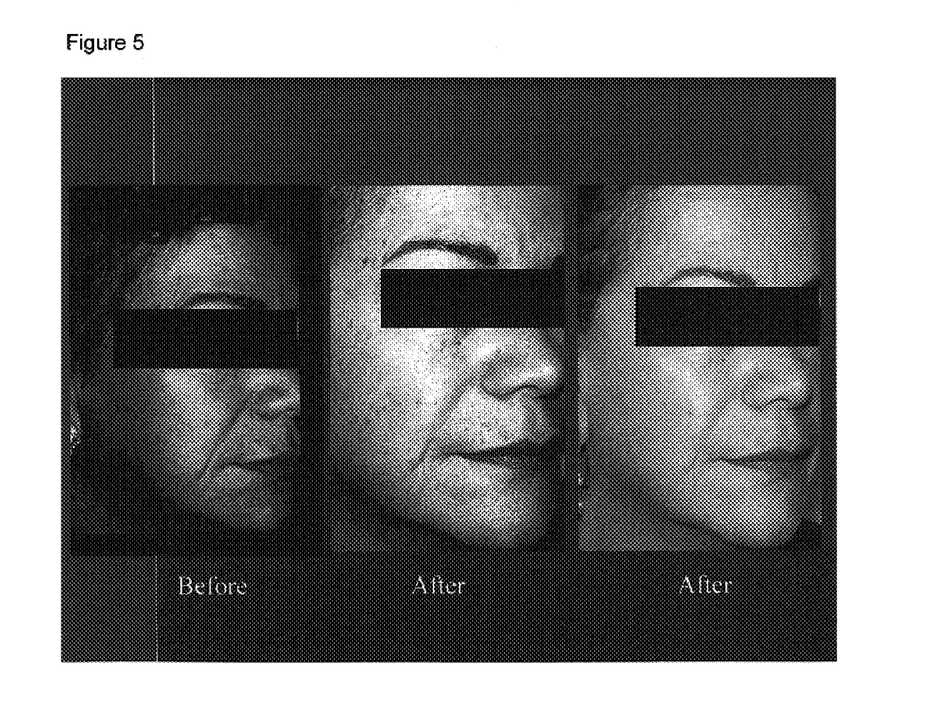
FIG. 5. Photographs taken before, after one month and after three months of application of an embodiment of the present invention.

As indicated by Examples 1 through 3, several formulations containing varying amounts of *vismia* and phytic acid have been produced and tested and have yielded amazing results. In FIG. 3, a patient is shown before and after one month of topical application of one embodiment of the present invention containing a combination of *vismia* and phytic acid. FIG. 4 provides a control study wherein a patient was provided with a formulation containing neither *vismia* nor phytic, similar to Example 6, and no improvements were demonstrated. FIG. 5 demonstrates the improvements yielded by three months of application of one embodiment of the present invention. Applicants have tested many different combinations and formulations containing *vismia*, phytic acid, arbutin, kojic acid and hydroquinone. None of these combinations have surpassed the results exhibited by the formulations containing both *vismia* and phytic acid.

The Examples and Figures have been provided for exemplary purpose only. It is to be understood that the invention is not limited to the embodiments disclosed in the Examples and Figures, but is intended to cover various modifications and equivalent arrangements included within the spirit of the invention, which are set forth in the appended claims, and which scope is to be accorded the broadest interpretation so as to encompass all such modifications and equivalent structures.

I claim:

1. A method of treating hyperpigmentation disorders in human skin comprising applying to human skin a topical composition comprising a mixture of *vismia* in an amount effective to lighten skin and phytic acid in an amount effective to lighten skin.

2. A method of treating hyperpigmentation disorders in human skin comprising applying to human skin a topical composition comprising:

a. about one to about five percent *vismia*, wherein about one to about five percent is an amount of *vismia* effective to lighten skin; and b. about one to about five percent phytic acid, wherein about one to about five percent is an amount of phytic acid effective to lighten skin.

3. A method of treating hyperpigmentation disorders in human skin comprising applying to human skin a topical composition comprising:
   a. about one to about five percent *vismia*, wherein about one to about five percent is an amount of *vismia* effective for lightening skin;
   b. about one to about five percent phytic acid, wherein about one to about five percent is an amount of phytic acid effective for lightening skin; and
   c. arbutin.

4. A method of treating hyperpigmentation disorders in human skin comprising applying to human skin a topical composition comprising:
   a. about one to about five percent *vismia*, wherein about one to about five percent is an amount of *vismia* effective for lightening skin;
   b. about one to about five percent phytic acid, wherein about one to about five percent is an amount of phytic acid effective for lightening skin; and
   c. kojic acid.

* * * * *